(12) United States Patent
Mohanty et al.

(10) Patent No.: US 7,432,239 B2
(45) Date of Patent: Oct. 7, 2008

(54) POLYOXYALKYLENE COMPOUND AND METHOD FOR MAKING

(75) Inventors: Dillip K. Mohanty, Mt. Pleasant, MI (US); Ajit Sharma, Mt. Pleasant, MI (US)

(73) Assignee: Central Michigan University Board of Trustees, Mt. Pleasant, MI (US)

( * ) Notice: Subject to any disclaimer, the term of this patent is extended or adjusted under 35 U.S.C. 154(b) by 433 days.

(21) Appl. No.: 11/141,836

(22) Filed: May 31, 2005

(65) Prior Publication Data

US 2005/0256032 A1 Nov. 17, 2005

Related U.S. Application Data

(63) Continuation of application No. 10/770,224, filed on Feb. 3, 2004, now abandoned.

(51) Int. Cl.
*A61K 38/00* (2006.01)
*A61K 38/02* (2006.01)
*C07K 1/00* (2006.01)
*C07K 1/107* (2006.01)

(52) U.S. Cl. ............................ 514/2; 530/300; 530/345
(58) Field of Classification Search ....................... None
See application file for complete search history.

(56) References Cited

U.S. PATENT DOCUMENTS

| | | | | |
|---|---|---|---|---|
| 4,774,178 A * | 9/1988 | Egerer et al. | ................... | 435/41 |
| 4,792,527 A * | 12/1988 | Uchida et al. | ............... | 436/507 |
| 5,286,637 A * | 2/1994 | Veronese et al. | ............ | 435/183 |
| 5,366,735 A | 11/1994 | Henry | | |
| 5,482,996 A * | 1/1996 | Russell et al. | ............... | 525/54.1 |
| 5,552,141 A * | 9/1996 | Ribi | ........................ | 424/184.1 |
| 5,648,506 A * | 7/1997 | Desai et al. | .................. | 549/510 |
| 6,048,720 A * | 4/2000 | Dalborg et al. | ............... | 435/219 |
| 6,080,404 A * | 6/2000 | Branham et al. | ......... | 424/140.1 |
| 6,280,745 B1 | 8/2001 | Flore et al. | | |
| 6,361,768 B1 * | 3/2002 | Galleguillos et al. | ..... | 424/70.12 |
| 6,706,821 B1 * | 3/2004 | Letchford | ................... | 525/302 |

OTHER PUBLICATIONS

J. Mack, et al. Letters in Peptide Scinece. (1999) 6, pp. 135-142.*
J. Mack, et al. Journal of Peptide Science. (2001) 7, pp. 338-345.*
K.A. Arendt, et al. Bioorg. Med. Chem. Letters (2003) 13, pp. 1683-1686.*
H.F. Gaertner and R.E. Offord. Bioconj. Chem. (1996) 7(1), pp. 38-44.*
Y. Inada, et al. Methods Enzymol. (1994) 242, pp. 65-90.*
J.M. Harris et al. J. Polymer Sci. (1994) 22, pp. 341-352.*
S. Kim and W.K. Paik. J. Biol. Chem. (1965) 240(12), pp. 4629-4634.*
K. Murray. Biochem. (1964) 3(1), pp. 10-15.*
Aldrich catalog, 2003-2004, p. 1404-1407, Pamam Dendrimers.
Shearwater Corp. catalog, 2001, see especially p. 10, (Group Six-Vinyl Derivatives).
Zalipsky, Bioconjugate Chem., 1995, 6, 150-165.
Henmanson, Bioconjugate Tech., 1996, Chapter 15.
Roberts, et al., Advanced Drug Delivery Reviews, S4 (2002), p. 459-476.
Bhadra, et.al., Int., J. Pharmaceutics 257 (2003) p. 111-124.
Zalipsky, et.al., Chemistry and Biological Applications of Peg, 1997, Chapter 1.
Pan, et.al., Macromolecules, 1999, 32, p. 5468-5470.
Nucci, et.al., Advanced Drug Delivery Reviews, 6, (1991), p. 133-151.
Liv et.al., J. Pol. Sc. Pt.A Pol. CHGM, vol. 37, (1999) p. 3492-3503.
Shorr, et.al., Eneyclopedia of Controlled Drug Delivery, vol. 1, p. 143-161, see especially p. 148-159.
Tomalia, et.al., Polymer Journal, 17, (1985) p. 117-132.

* cited by examiner

*Primary Examiner*—Andrew D Kosar
(74) *Attorney, Agent, or Firm*—Robert L. McKellar; McKellar IP Law, PLLC

(57) ABSTRACT

A process for forming a conjugate of a polyoxyalkylene polymer, such as polyethylene glycol, with a compound containing an amine group(s) and/or a sulfide group(s) by reacting the compound with an acrylate terminated polyoxyalkylene, such as polyethylene glycol terminated at one end with acrylate or methacrylate and terminated at the other end with a methoxy group. The reaction is believed to be a Michael addition. When the compound contains primary amine groups, such as the surface primary amine groups of a PAMAM dendrimer, it is usually desirable to convert the primary amine groups to secondary amine groups before the reaction with the acrylate terminated polyoxyalkylene.

6 Claims, No Drawings

POLYOXYALKYLENE COMPOUND AND METHOD FOR MAKING

This application is a Continuation of U.S. application Ser. No. 10/770,224 filed Feb. 3, 2004 now abandoned.

BACKGROUND

The instant invention is in the field of chemical compounds comprising polyoxyalkylene sub-structures such as polyethylene glycol sub-structures. The instant invention also relates to methods for producing chemical compounds comprising polyoxyalkylene sub-structures.

Biologically active compounds comprising polyoxyalkylene sub-structures can provide enhanced biocompatibility for the compound, See, for example, U.S. Pat. No. 5,366,735 and U.S. Pat. No. 6,280,745. A review of this subject by Zalipsky, in Bioconjugate Chem., 1995, 6, p 150-165, identified polyethylene glycol as one of the best biocompatible polymers to conjugate with a biologically active compound, such as a drug, a protein, or an enzyme, to produce a conjugate having improved properties such as compatible solubility characteristics, reduced toxicity and reduced immunogenicity.

Polyethylene glycol (PEG) is a linear or branched polyoxyalkylene terminated at the ends thereof with hydroxyl groups and generally represented by the formula: HO—$(CH_2CH_2O)_n$—$CH_2CH_2$—OH. As discussed by Henmanson in Chapter 15 of Bioconjugate Techniques (1966), monomethoxy polyethylene glycol (mPEG) generally represented by the formula: $CH_3O$—$(CH_2CH_2O)$—$CH_2CH_2$—OH, is usually used to prepare a polyethylene glycol conjugate with a biologically active compound typically by way of a coupling reaction between an amine group of the biologically active compound and an amine receptive derivative, such as trichloro-s-triazine activated mPEG, formed via the remaining terminal hydroxyl group of the monomethoxy polyethylene glycol. An acrylate terminated PEG is offered commercially by Shearwater Corporation (Huntsville, Ala.) for vinyl polymerization or co-polymerization to produce graft polymers or cross-linked materials with excellent properties for biomaterial applications.

More recently, so called "second generation" PEGylation chemistry has been developed to, for example, minimize problems of diol impurity contamination of mPEG, to increase the molecular weight of the polyoxyalkylene sub-structure and to increase stability of the conjugate, see Roberts et al., Advanced Drug Delivery Reviews 54 (2002) p 459-476.

Dendrimers are hyperbranched, uniformly distributed structures, having, at least ideally, definite molecular weight, shape and nanometer size characteristics. Dendrimers were discovered by inventors at the Dow Chemical Company, see Polym. J. 17 (1985) p 117-132. Dendrimers have been widely studied as a drug delivery means, see for example Knusli et al., J. Haematology, 82, 654 (1992). Dendrimers carrying the anti cancer drug 5-fluorouracil have been PEGylated to reduce hemolytic toxicity, drug leakage and macrophageal uptake while improving stability and efficacy, see Bhadra et al., International Journal of Pharmaceutics 257 (2003) p 111-124.

PAMAM dendrimers are the most common type of dendrimer and are commercially available from Aldrich (Milwaukee, Wis.) in the form of various "generations". PAMAM dendrimers are made by a successive Michael addition synthesis scheme involving the reaction of an acrylate group with an amine group. The so called "Generation 0" PAMAM dendrimer has the following formula:

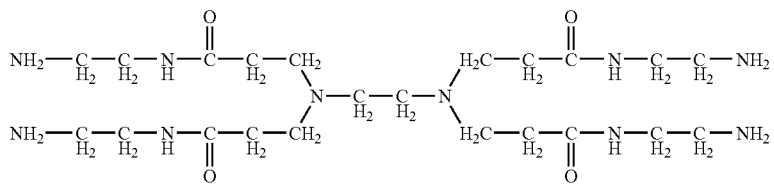

The above Generation 0 PAMAM dendrimer has a molecular weight of about 517 grams per mole. A Generation 1 PAMAM dendrimer has a molecular weight of about 1,430 grams per mole and has eight terminal primary amine groups. A Generation 2 PAMAM dendrimer has a molecular weight of about 3,256 grams per mole and has sixteen terminal primary amine groups. A Generation 10 PAMAM dendrimer has a theoretical molecular weight of almost 935 kilograms per mole and in theory has 4096 primary amine groups on the surface of the dendrimer.

Despite the significant advances that have been made in the field of methods for the PEGylation of biologically active compounds, and more generally in the field of methods for the conjugation of polyoxyalkylene sub-structures with biologically active compounds, the existing methods generally require multiple reactions and extensive purification of the product. It would be an advance in this art if a process was discovered that required only one reaction step and produced no by-products.

SUMMARY OF THE INVENTION

The method of the instant invention is a solution, at least in part, to the above described problems of the prior art. The instant invention provides a one step pegylation method that ideally produces no by-products. In addition, the method of the instant invention can be practiced at room temperature and under conditions such as solvent compatibility that are mild relative to maintenance of biological activity. In one embodiment, the instant invention is applicable to biologically active compounds containing an amine group. In another embodiment, the instant invention is applicable to biologically active compounds containing a sulfide group. The biologically active compound is reacted with an acrylate terminated polyoxyalkylene, such as $H_2C\!=\!CH$—CO—O-PEG-O—$CH_3$ in a one step process to produce novel conjugates having many if not all of the benefits of the prior art conjugates.

More specifically, the instant invention is a method for preparing a compound corresponding to the formula:

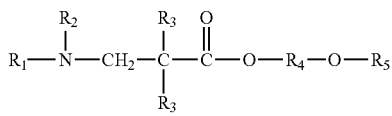

where $R_1$ is an organic radical
where $R_2$ is H or an organic radical
where $R_3$ is H or an organic radical
where $R_4$ is a polyoxyalkylene radical
and where $R_5$ is an organic radical or H, comprising the step of: reacting A with B, wherein A is $R_1$—N—$R_2$ and wherein

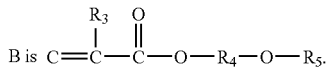

In another embodiment, the instant invention is a method for preparing a compound corresponding to the formula:

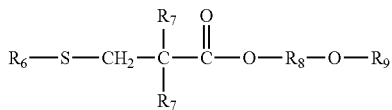

where $R_6$ is an organic radical
where $R_7$ is H or an organic radical
where $R_8$ is a polyoxyalkylene radical
and where $R_9$ is an organic radical or H, comprising the step of: reacting D with E, wherein D is $R_6$—S and wherein

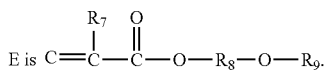

In addition, the invention comprises the compounds created by the reactions described Supra.

DETAILED DESCRIPTION OF THE INVENTION

In general, the process of the instant invention can be conducted at room temperature. Infrared (IR) spectra are obtained using a thin film on a sodium chloride plate. Spectra are recorded using a Nicolet 20DXB Fourier Transform (FT-IR) Spectrometer and absorption is reported in wave number ($cm^{-1}$). IR spectra cover the range 1000-4000 $cm^{-1}$.

Proton nuclear magnetic resonance spectra and carbon-13 nuclear magnetic resonance spectra are recorded for solutions in appropriate solvents containing tetramethyl-silane in case of chloroform and methanol and 3(trimethylsilyl)propane Sulfonic acid sodium salt (DSS) in case of Deuterium Oxide as internal standard using a General Electric QE-300 NMR spectrometer. The NMR shifts are reported in parts per million ($\delta$, PPM). The following standard abbreviations were used in describing NMR data: s=singlet, d=doublet, t=triplet, q=quartet, m=multiplet.

Mass Spectra are obtained by using a Hewlett-Packard Model 5995A gas Chromatograph/Mass Spectrometer with an ionizing potential of 70 electron volts.

Starting Materials

1. PAMAM Dendrimer (Generation=0)
    Source: Aldrich Chemical; Structure:

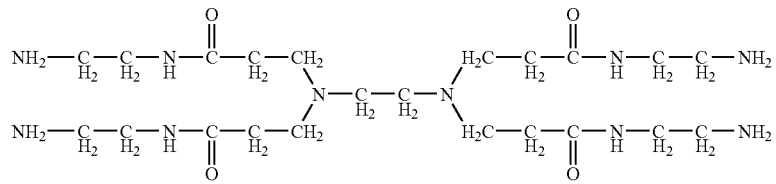

The structure above may also be represented

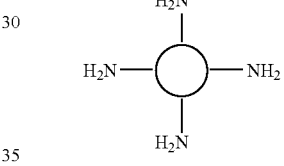

Note: PAMAM Dendrimer is purchased in 20% solution in methanol and used without further purification.

2. Poly Ethylene Glycol Methyl Ether Acrylate
    Source: Aldrich Chemical Company
    Structure:

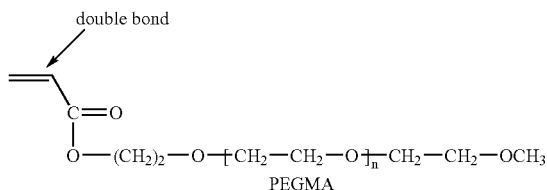

Used without further purification.
A PEG chain may be represented:

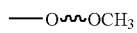

3. Ethylene diamine
    Source: Aldrich Chemical Company
    Structure:

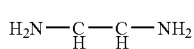

Purification procedure: Ethylene diamine was distilled over $CaH_2$.

4. Benzaldehyde
   Source: Fisher Scientific
   Structure:

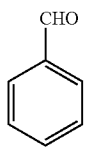

Purification procedure: Benzaldehyde (about 75 mL) was placed in a separatory funnel. It was washed with 10% $NaCO_3$ until no more $CO_2$ evolved. Saturated NaCl solution was added to the solution. The solution was then washed with a saturated solution of $Na_2SO_3$ followed by washing with water. The organic layer was collected and dried with $MgSO_4$. The organic layer was filtered and then distilled under vacuum.

5. Acetophenone
   Source: Fisher Scientific
   Structure:

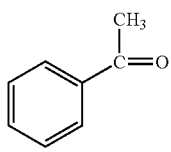

used without further purification.

6. Propylamine
   Source: Aldrich Chemical Company
   Structure:

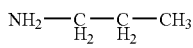

It was distilled over $CaH_2$ before use.

7. N-ethyl N-benzyl amine
   Source: Aldrich Chemical Company
   Structure:

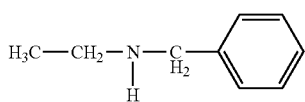

used without further purification.

8. Methanol
   Source: Burdick and Jackson
   Structure: $CH_3OH$ used without further purification.

9. Molecular Sieve (Size 3A)
   Source: EM Science

1. Model Reaction
   Molecular Weight: 1108 g/mole

Reaction Scheme:

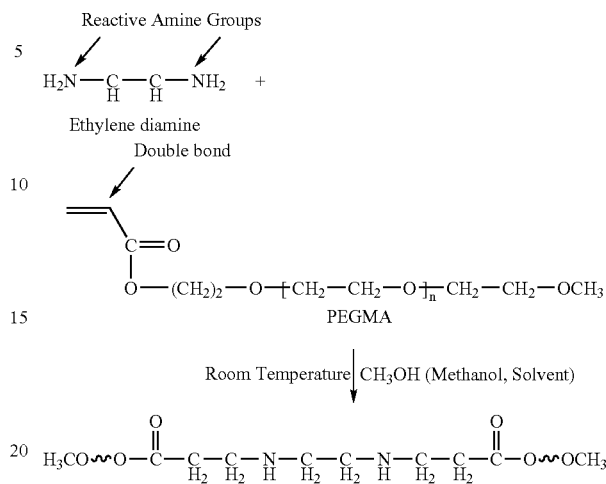

Procedure: Ethylene diamine (0.5714 g, $0.9525*10^{-3}$ moles) and PEGMA (1 gm, $1.905*10^{-3}$) and 3 mL of methanol were added to a clean and dry vial. The vial was capped and allowed to shake for 2 hours. Methanol was removed under vacuum at room temperature. The product was a sticky solid.

Spectral Data:
IR: $cm^{-1}$
3514.3, 2873.2, 1723.8, 1656.3, 1462.3, 1449.6, 1407.5, 1344.2, 1293.6 1276.7, 1243.0, 1192.4, 1108.0

$^1$H NMR: ($\delta$ ppm) in $CD_3OD$
2.52(m), 2.69(s), 2.84(t), 3.35(s), 3.53(m), 3.62(d), 3.66 (m), 4.70(t)

$^{13}$C NMR: ($\delta$ ppm)
33.33, 34.76, 45.67, 52.10, 53.92, 59.08, 62.17, 64.68, 70.05, 71.31, 72.91, 73.64

2. PAMAM Dendrimer (Generation=0)–PEGMA (¼ Equivalent) Conjugate
   Molecular weight: 1041 g/mole
   Reaction Scheme:

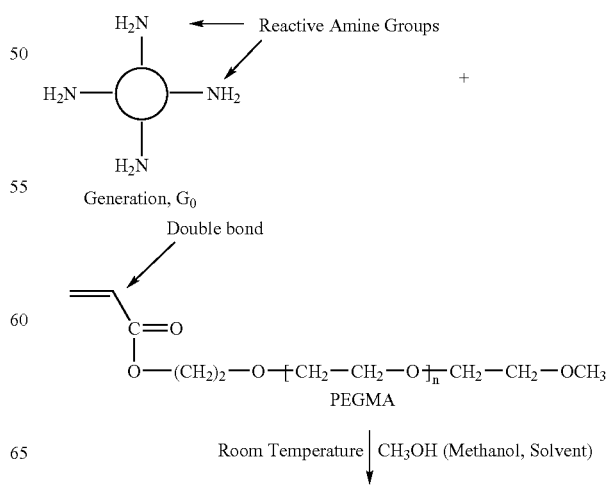

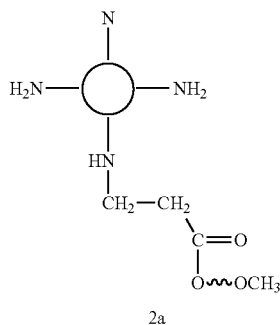

2a

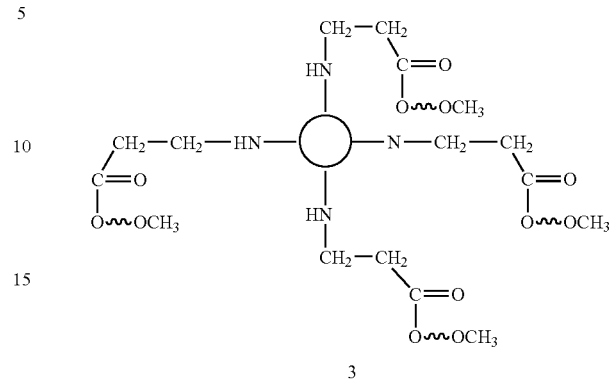

3

Procedure: 1 mL of G$_0$ solution (20% solution in methanol) is taken in a clean dry vial. PEGMA (0.0254 g, 0.00019 moles) is added to the vial along with the 2 mL methanol. The vial is capped tightly and allowed to shake for about 3 hours. The methanol is removed after the reaction is over. The product is a sticky solid.

Spectral Data $^1$H NMR: ($\delta$ ppm) in D$_2$O
2.42(t), 2.60(s), 2.65(t), 2.70(t), 3.24(t), 3.28(s), 3.40(s), 3.62(m), 3.65(s), 3.80(m), 4.24(t).

$^{13}$C NMR: ($\delta$ ppm)
32.59, 36.41, 36.65, 40.96, 41.13, 45.07, 46.97, 48.80, 49.06, 49.96, 58.01, 60.30, 69.41, 69.54, 69.63, 70.94, 71.69, 174.92, 175.03, 175.21, 175.30, 175.97, 180.62, 180.70

3. PAMAM Dendrimer (Generation=0)–PEGMA (4 Equivalents) Conjugate
Molecular weight: 2613 g/mole Reaction Scheme:

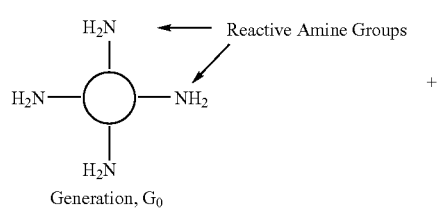

Generation, G$_0$

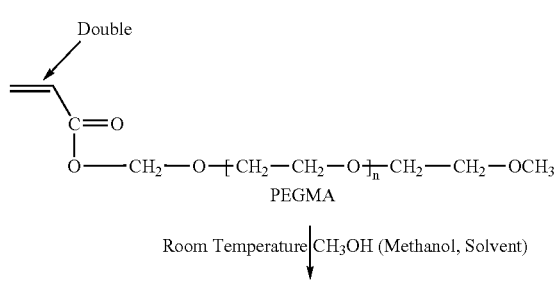

Procedure: 1 mL of G$_0$ solution (20% solution in methanol) is taken in a clean dry vial. PEGMA (0.1016 g, 0.00076 moles) is added to the vial along with the 2 mL methanol. The vial is capped tightly and allowed to shake for about 3 hours. The methanol is removed after the reaction is over. The product is a sticky solid.

Spectral Data:

$^1$H NMR: ($\delta$ ppm) in D$_2$O
2.42(t), 2.59(m), 2.70(t), 2.82(m), 3.29(t), 3.37(s), 3.62(m), 3.69(s), 3.80(m), 4.30(d)

$^{13}$C NMR: ($\delta$ ppm)
21.65, 33.90, 34.52, 34.90, 38.52, 39.21, 45.70, 47.05, 49.29, 49.29, 49.68, 50.82, 51.19, 51.35, 52.28, 53.26, 53.88, 54.01, 54.72, 54.90, 56.92, 60.55, 62.84, 66.43, 70.93, 71.95, 72.08, 72.17, 73.49, 74.23, 176.60, 176.70, 177.06, 177.51, 177.83, 180.58.

4. PAMAM Dendrimer (Generation=0)–PEGMA (2 Equivalents)–Benzaldehyde (3 Equivalents)
Molecular weight: 1305 g/mol Reaction Scheme:

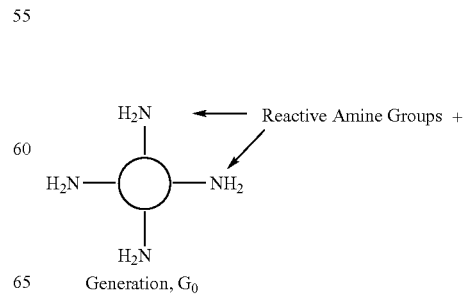

Generation, G$_0$

-continued

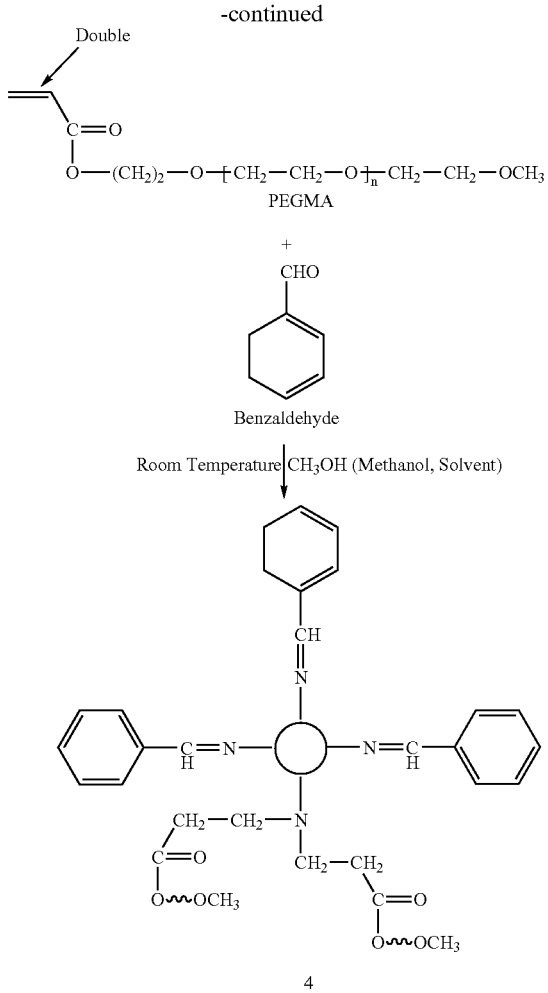

4

Procedure: 2 mL of $G_0$ and Benzaldehyde (0.24603 g, 0.00232107 moles) are placed in a clean dry vial, capped tightly and allowed to shake for about 24 hours. PEGMA (0.40612 g, 0.000774 moles) is added thereafter. The vial is allowed to shake for about 100 hours. The methanol is removed under vacuum at room temperature. The product is a sticky solid.

Spectral Data

IR: $cm^{-1}$ 1107.4, 1196.6, 1273.6, 1293.9, 1350.6, 1407.3, 1451.9, 1723.5, 2865.6

$^1$H NMR: ($\delta$ ppm) in $CD_3OD$ 2.30 (m), 2.45 (m), 2.60 (m), 2.70 (m), 2.95 (m), 3.34 (s), 3.62 (s), 4.20 (d), 7.40 (m), 7.75 (m), 7.795 (m), 8.30 (d)

$^{13}$C NMR: ($\delta$ ppm)

33.50, 33.63, 33.83, 38.47, 39.11, 40.74, 41.02, 45.14, 50.41, 50.85, 51.76, 52.27, 53.65, 59.07, 60.99, 62.14, 64.76, 71.27, 71.30, 71.45, 72.87, 73.61, 128.78, 129.40, 129.78, 130.26, 131.40, 132.21, 137.01, 165.20, 173.86, 174.09, 174.63, 174.95

5. PAMAM Dendrimer (Generation=0)-PEGMA (2 equivalents)-Acetophenone (3 Equivalents)

Molecular weight: 1347 g/mole

Procedure: 1 mL of $G_0$ and Acetophenone (0.1395 g, 0.0021161 moles) are placed in a clean dry vial. 2 scoops of molecular sieve were added to the vial. It was capped tightly and allowed to shake for about 24 hours. PEGMA (0.4062 g, 0.000774 moles) was added thereafter and allowed to shake for about 100 hours. The methanol was removed under pump at room temperature. The product is a sticky solid.

Spectral Data

IR: $cm^{-1}$ 1036.2, 1107.4, 1139.8, 1196.6, 1251.3, 1273.6, 1295.9, 1348.6, 1407.3, 1447.3, 1597.8, 1634.3, 1658.6, 1723.5, 2865.6, 3514.1.

$^1$H NMR: ($\delta$ ppm) in $D_2O$ 2.22(s), 2.43(t), 2.57(m), 2.65(s), 2.70(m), 2.80(d), 3.28(t), 3.30(m), 3.35(s), 3.38(s), 3.70(s), 3.63(m), 7.46(q), 7.55(t), 7.69(m), 7.98 (d)

$^{13}$C NMR: ($\delta$ ppm)

17.65, 21.76, 28.42, 28.92, 32.90, 34.05, 35.21, 36.11, 41.12, 42.21, 42.62, 42.98, 46.12, 47.60, 49.61, 51.51, 52.61, 54.87, 57.03, 60.70, 63.00, 72.10, 72.23, 73.63, 74.37, 131.18, 131.47, 136.81, 139.00, 165.00, 177.50, 177.89, 177.80, 182.64.

6. Model Reaction a. Schiff Base Formation by the Reaction Between Propylamine and Acetophenone;

Molecular weight: 161 g/mol

Reaction Scheme:

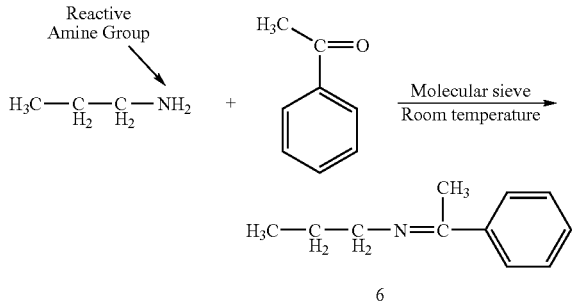

6

Procedure: Acetophenone (1.006 g, 0.00779 moles) and Propylamine (2.510 g, 0.0425 moles) are added in a clean dry vial. About 4 scoops of warm molecular sieve are added to the vial and capped tightly. The vial is allowed to shake for about 96 hours. The solution is collected using the solvent $CH_2Cl_2$ and dried over $MgSO_4$. The solution is filtered through celite and dried under vacuum at room temperature.

Spectral Data

IR: $cm^{-1}$ (intensity)

1027.04, 1074.89, 1180.02, 1376.10, 1446.25, 1492.57, 1578.19, 1634.03, 2872.57, 2930.89, 2958.92, 3024.00, 3058.14, 3078.24.

MS: m/e (% of base)

162, 16, 160, 146, 132, 104, 91 (100%), 77

$^1$H NMR: ($\delta$ ppm) in $CDCl_3$ 1.01 (t), 1.78 (q), 2.20 (s), 3.42 (t), 7.34 (m), 7.76 (m).

$^{13}$C NMR ($CD_3OD$): (a ppm)

12.07, 15.31, 24.05, 29.05, 53.85, 54.99, 77.00, 125.61, 128.02, 129.10, 141.34, 164.67, 165.41, 168.22.

b. Reduction of Imine:
Molecular weight: 163 g/mole

Reaction Scheme $$H_3C-\underset{H_2}{C}-\underset{H_2}{C}-N=\underset{CH_3}{\overset{CH_3}{C}}-C_6H_5 \xrightarrow{NaBH_3CN}$$

6

$$H_3C-\underset{H_2}{C}-\underset{H_2}{C}-\underset{H}{\overset{H}{N}}-\underset{H}{\overset{CH_3}{C}}-C_6H_5$$

7

Procedure: Product (1.348 g, 0.008373 moles) of the above reactant is placed in a clean dry vial. NaBH3CN (0.350 g, 0.00557 moles) was taken in a clean dry vial and about 1.5 mL of methanol is added to that in order to make a clear solution. The solution is added to the reaction vial and capped tightly. The vial is allowed to shake for about 72 hours at room temperature. After 72 hours about 6(N)HCl is added drop by drop until the pH is <2. Then the solution is brought to a pH of >10 with 10% NaOH solution. The opaque solution is then dried over $MgSO_4$, filtered through celite and dried over vacuum at room temperature.

Spectral Data

IR: $cm^{-1}$ (intensity)
1027.53, 1071.61, 1286.90, 1370.64, 1450.87, 1492.02, 1601.13, 2871.74, 2931.94, 2959.54, 3025.48, 3062.21.

MS: m/e (% of base)
163, 162, 148, 134, 105 (100%), 77

$^1$H NMR: ($\delta$ ppm) in $CD_3OD$
0.94 (t), 3.66 (d), 2.69 (m), 2.88 (m), 3.34 (s), 4.35 (q), 4.93 (s), 7.47 (m).

$^{13}$C NMR: ($\delta$ ppm) in $CD_3OD$
9.87, 18.30, 19.36, 58.14, 127.15, 129.05, 129.16, 136.54.

c. N-EthylBenzyl amine-PEGMEA conjugates:

Structure:

Reactive Secondary Amine Group $$H_3C-\underset{H_2}{C}-\underset{H}{\overset{H}{N}}-\underset{H_2}{C}-C_6H_5 \quad +$$

N ethyl benzyl amine

-continued

Double bond
$$\overset{\nearrow}{CH_2=CH-\underset{O}{\overset{O}{\|}}C}-O-(CH_2)_2-O-[CH_2-CH_2-O]_n-CH_2-CH_2-OCH_3$$

PEGMA $\downarrow$ Room Temperature | $CH_3OH$ (Methanol, Solvent)

$$H_3C-\underset{H_2}{C}-\underset{|}{\overset{}{N}}-\underset{H_2}{C}-C_6H_5$$
$$\underset{CH_2}{|}$$
$$\underset{CH_2}{|}$$
$$O=C$$
$$|$$
$$O\sim\sim OCH_3$$

8

Procedure: PEGMA (1 g, 0.00191 moles), N-ethyl benzylamine (0.258 g, 0.00191 moles) and methanol are placed in a clean dry vial. The vial is capped tightly and allowed to shake for about 72 hours. The methanol is evaporated off under vacuum at room temperature.

Spectral Data $^1$H NMR: ($\delta$ ppm) in $CD_3OD$
1.03 (t), 2.48 (q), 2.77 (t), 3.34 (s), 3.57 (m), 3.82 (m), 4.19 (t), 4.28 (t), 7.23 (m), 7.29 (d).

$^{13}$C NMR: ($\delta$ ppm) in $CD_3OD$
11.96, 32.91, 33.05, 48.06, 49.57, 52.02, 58.80, 59.08, 62.18, 64.66, 64.81, 71.32, 71.51, 72.92, 73.64, 128.06, 129.21, 130.12, 140.15, 167.44, 174.10, 174.63.

7. Pegylation of Reduced PAMAM Dendrimer (Generation=0)–Benzaldehyde (4 Equivalents) Conjugates:
Molecular weight: 2977 g/mole Reaction Scheme:

a.

Reactive Amine Groups $$H_2N-\bigcirc-NH_2$$
$$H_2N \quad \quad H_2N$$

Generation, $G_0$

+

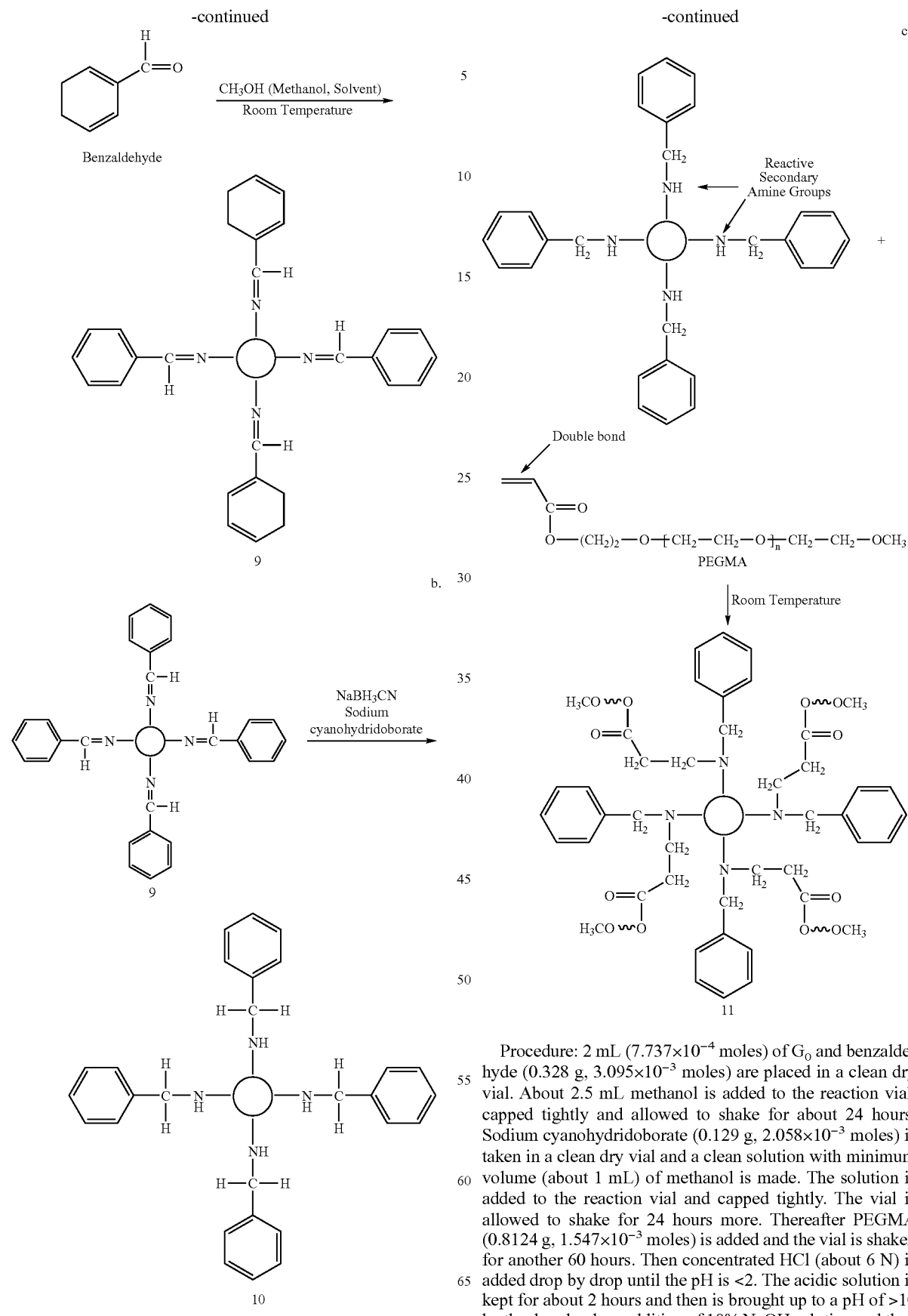

Procedure: 2 mL (7.737×10⁻⁴ moles) of $G_0$ and benzaldehyde (0.328 g, 3.095×10⁻³ moles) are placed in a clean dry vial. About 2.5 mL methanol is added to the reaction vial, capped tightly and allowed to shake for about 24 hours. Sodium cyanohydridoborate (0.129 g, 2.058×10⁻³ moles) is taken in a clean dry vial and a clean solution with minimum volume (about 1 mL) of methanol is made. The solution is added to the reaction vial and capped tightly. The vial is allowed to shake for 24 hours more. Thereafter PEGMA (0.8124 g, 1.547×10⁻³ moles) is added and the vial is shaken for another 60 hours. Then concentrated HCl (about 6 N) is added drop by drop until the pH is <2. The acidic solution is kept for about 2 hours and then is brought up to a pH of >10 by the drop by drop addition of 10% NaOH solution and then dried over MgSO$_4$ and filtered through celite. The methanol is then evaporated under vacuum at room temperature.

Spectral Data:

A. G$_0$+4Benzaldehyde $^1$H NMR: ($\delta$ ppm) in CD$_3$OD
2.23 (t), 2.35 (s), 2.59 (t), 3.34 (s), 3.48 (t), 3.66 (t), 4.92 (s), 5.46 (s), 7.40 (m), 7.53 (t), 7.60 (t), 7.63 (t), 7.65 (t), 7.73 (m), 7.84 (m), 7.86 (t), 8.25 (s), 10.00 (s).

$^{13}$C NMR: ($\delta$ ppm) in CD$_3$OD
32.56, 34.24, 35.93, 39.10, 40.94, 42.80, 50.93, 51.784, 52.65, 53.58, 59.06, 59.11, 60.86, 61.05, 62.67, 62.73, 128.28, 128.62, 128.92, 129.02, 129.50, 129.59, 130.39, 130.72, 130.73, 130.95, 131.05, 131.15, 131.55, 131.63, 131.71, 133.08, 133.18, 133.28, 134.35, 134.45, 136.83, 136.93, 137.07, 163.94, 166.04, 174.66, 192.77, 192.83, 192.90, 195.09, 195.15, 195.21.

B. G$_0$+4Benzaldehyde+NaBH$_3$CN $^1$H NMR: ($\delta$ ppm) in CD$_3$OD
2.54 (m), 2.53 (m), 2.73 (m), 2.86 (m), 3.34 (s), 3.38 (s), 3.59 (s), 3.76 (s), 4.622 (s), 4.89 (s), 5.01 (t), 5.11 (m), 7.34 (m), 7.54 (m), 7.76 (m), 8.35 (m)

$^{13}$C NMR: ($\delta$ ppm) in CD$_3$OD
34.67, 38.41, 39.85, 42.01, 42.96, 47.43, 51.23, 52.33, 53.71, 54.15, 57.10, 59.42, 65.19, 116.96, 120.39, 127.92, 128.13, 128.51, 128.76, 128.89, 129.26, 129.43, 129.66, 129.87, 135.37, 136.62, 139.00, 140.63, 142.63, 174.51, 174.60, 175.02, 175.09, 175.16.

C. G$_0$+4Benzaldehyde+NaBH$_3$CN+PEGMEA

IR: cm$^{-1}$ (intensity)
11091, 1198.77, 1249.93, 1293.76, 1350.91, 1452.86, 1542.64, 1564.72, 1630.09, 1658.20, 1736.78, 2871.20.

$^1$H NMR: ($\delta$ ppm) in DMSO-d$_6$
2.15 (s), 2.42 (t), 2.49 (m), 2.58 (s), 2.60 (d), 3.08 (d), 3.15 (s), 3.22 (s), 3.41 (t), 3.49 (s), 3.53 (s), 4.47 (d), 4.66 (t), 7.21 (m), 7.29 (m), 7.41 (m), 7.54 (m), 7.88 (m).

$^{13}$C NMR: ($\delta$ ppm) in DMSO-d$_6$
31.86, 32.04, 33.21, 36.48, 48, 61, 48.86, 49.79, 51.25, 52.30, 57.57, 58.08, 60.20, 62.87, 69.60, 69.80, 71.30, 72.35, 126.43, 126.63, 126.81, 127.31, 127.51, 128.70, 128.17, 128.51, 128.71, 139.32, 142.57, 171.21, 172.52.

8. Pegylation of Reduced PAMAM Dendrimer (Generation=0) Acetophenone (4 Equivalents) Conjugates:

Molecular weight: 3033 g/mole

Reaction Scheme:

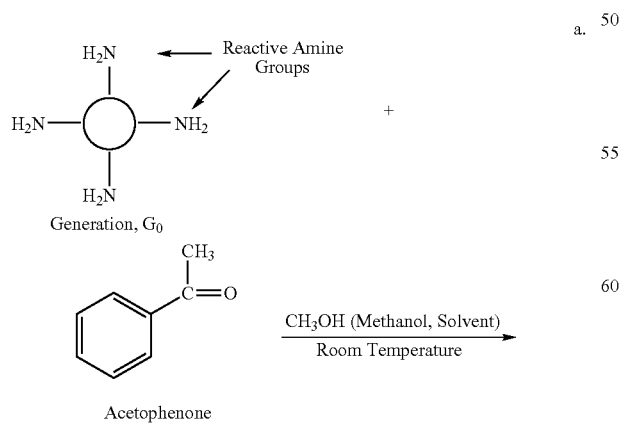

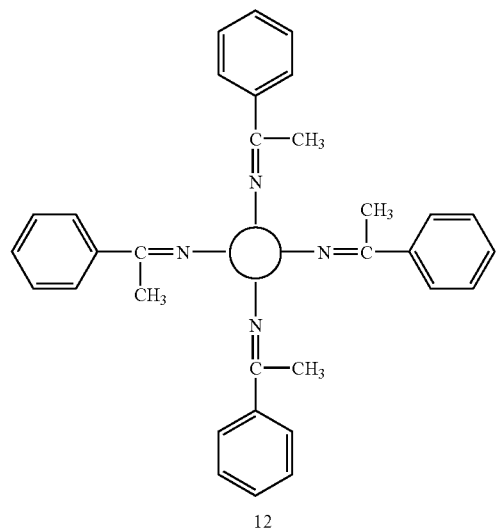

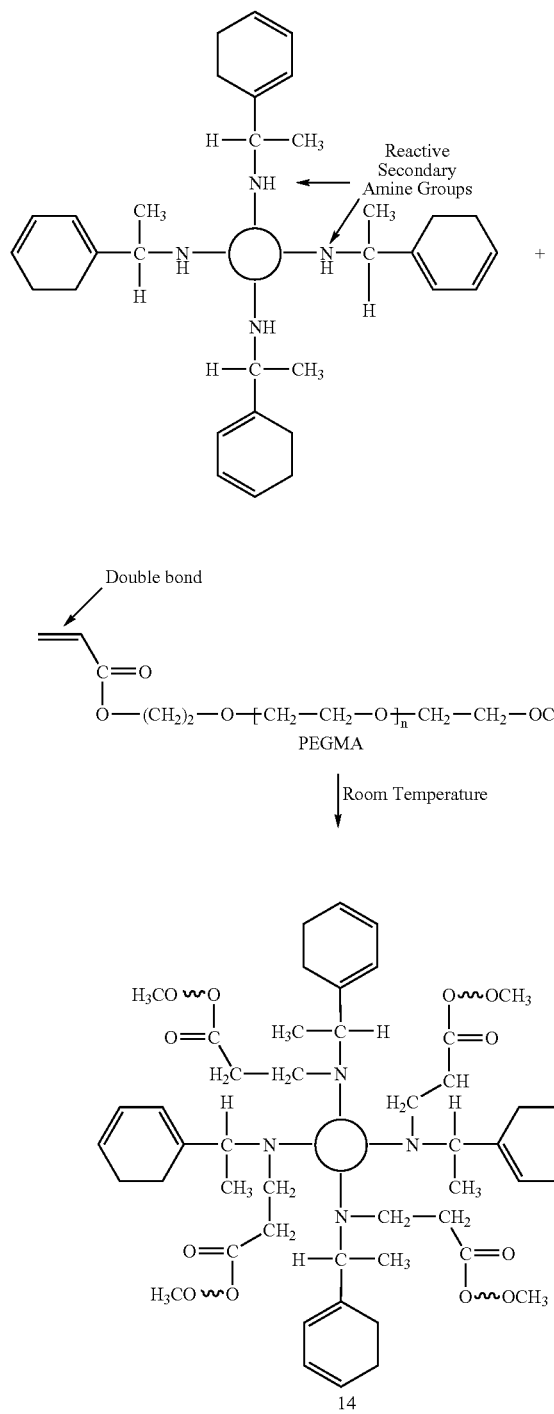

Procedure: 2 mL (7.737×10$^{-4}$ moles) of $G_0$ and acetophenone (0.372 g, 3.095×10$^{-3}$ moles) are placed in a clean dry vial. About 2.5 mL methanol is added to the reaction vial along with 3 scoops of molecular sieve (3A), capped tightly and allowed to shake for about 24 hours. Sodium cyanohydridoborate (0.129 g, 2.058×10$^{-3}$ moles) is taken in a clean dry vial and a clean solution with minimum volume (about 1 mL) of methanol is made. The solution is added to the reaction vial and capped tightly. The vial is allowed shake for 72 hours more. Thereafter PEGMA (0.8124 g, 1.547×10$^{-3}$ moles) is added and the vial is allowed to shake for another 120 hours. The solution turns to a pink color. Then concentrated HCl (about 6 N) is added drop by drop until the pH is <2. The acidic solution is kept for about 2 hours and then is brought up to a pH of >10 by the drop by drop addition of 10% NaOH solution, dried over MgSO$_4$ and filtered through celite. The methanol is then evaporated under vacuum at room temperature.

Spectral Data:

A. $G_0$+4 Acetophenone:

$^1$H NMR: (δ ppm) in CDCl$_3$ 2.20 (m), 2.65 (d), 2.57 (t), 2.62 (S), 2.72 (t), 3.22 (m), 3.34 (m), 3.49 (d), 3.55 (t), 7.07 (m), 7.27 (s), 7.35 (m), 7.47 (t), 7.59 (t), 7.72 (m), 7.98 (d).

$^{13}$C NMR: (δ ppm) in CDCl$_3$ 16.19, 16.27, 34.03, 34.13, 34.31, 50.36, 50.68, 50.80, 51.38, 51.54, 51.69, 76.58, 77.42, 125.84, 126.56, 128.17, 129.62, 133.10, 140.83, 167.14, 167.32, 172.68, 172.77, 173.01.

B. $G_0$+4 Acetophenone+NaBH$_3$CN $^1$H NMR: (δ ppm) in CD$_3$OD 1.37 (m), 1.43 (d), 2.36 (m), 2.51 (t), 2.60 (s), 2.72 (m), 2.85 (t), 3.27 (m), 3.30(m), 3.37 (s), 3.78 (m), 7.22 (m), 7.31(m), 7.47 (m), 7.49 (d), 7.52 (d), 7.58 (d), 7.98 (d), 8.01 (t).

$^{13}$C NMR: (δ ppm) in CD$_3$OD 23.99, 25.62, 34.57, 39.96, 41.10, 42.918, 47.66, 49.85, 51.19, 52.29, 59.12, 70.81, 126.42, 127.77, 128.05, 128.15, 129.24, 129.56, 145.93, 147.80, 174.99, 175.21.

C. $G_0$+4 Acetophenone+NaBH$_3$CN+PEGMEA

IR: cm$^{-1}$ (intensity)

1101.38, 1199.40, 1249.53, 1288.77, 1350.85, 1452.80, 1580.67, 1630.78, 1657.81, 1736.70, 2873.04.

$^1$H NMR: (δ ppm) in DMSO-d$_6$ 1.18 (d), 1.28 (d), 2.15 (s), 2.36 (t), 2.49 (t), 2.56 (s), 2.65 (t), 3.03 (t), 3.14 (d), 3.21 (s), 3.40 (t), 3.48 (s), 3.54 (m), 4.22 (q), 4.68 (t), 7.64 (d), 7.27 (m), 7.87 (m), 8.07 (m).

$^{13}$C NMR: (δ ppm) in DMSO-d$_6$ 24.64, 32.11, 33.33, 36.72, 46.76, 48.62, 48.98, 49.98, 49.98, 51.29, 52.34, 57.42, 58.12, 60.22, 69.64, 69.84, 71.34, 72.38, 125.35, 126.54, 127.48, 128.03, 128.23, 146.24, 171.35, 171.43, 172.55.

Analysis of spectral data especially the $^1$H NMR analysis of the pegylated PAMAM dendrimer revealed the fact that the double bond of PEGMA is allowed to react with the terminal amine groups of PAMAM dendrimer qualitatively. However, it was observed that the desired product, 3, is not apparently formed. Detailed analysis of NMR spectra suggested that although 3 forms first, it is rapidly converted into 15 in the presence of solvent methanol. A considerable amount of compound 15 gets converted back to 3 during the removal of methanol at the completion of the reaction. Moreover, both 3 and 15 are unstable in presence of water and are hydrolyzed rapidly to 16. The mechanism is believed to be a series of substitution reactions described below. The intra molecular hydrogen bond appears to be playing an important role to facilitate above described reactions.

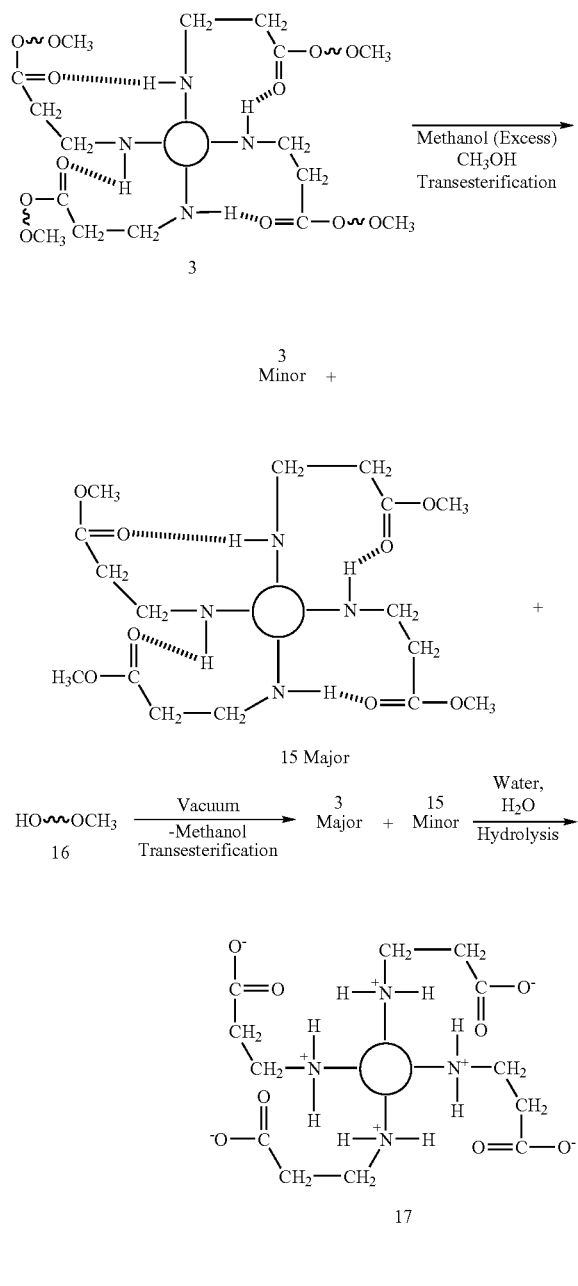

Denotes H-bonding

An examination of the above scheme clearly demonstrates the proposition that the hydrogen atom on the nitrogen atom plays a pivotal role in the production of 15 and 17, instead of the desired product 3. Furthermore, it is suspected that the dendrimer molecule under investigation can speed up transesterification and hydrolysis processes readily. It is also suspected that transesterification and hydrolysis processes occurs for quarter as well as per pegylation. It is observed from the NMR spectrum that the intensity ratio of the peaks corresponding to the methoxy groups ($OCH_3$) of methanol and compound 16 was changed with the time upon the addition of the water. When water is added to the pegylated PAMAM dendrimer, the changes of the intensity ratio of the absorbance correspond to methoxy groups of methanol and compound 16 can be monitored by $^1H$ NMR spectrum. The ratio Vs time is noted as illustrated in Table 1 below. It is suspected from the data that rates of hydrolysis follow the same trend.

TABLE 1

| Time(min) | Ratio | 1/Rato |
|---|---|---|
| 7 | 0.48 | 2.1 |
| 19 | 0.47 | 2.13 |
| 22 | 0.51 | 1.97 |
| 27 | 0.65 | 1.54 |
| 31 | 0.41 | 2.44 |
| 35 | 0.57 | 1.74 |
| 39 | 0.66 | 1.51 |
| 44 | 0.53 | 1.87 |
| 48 | 0.67 | 1.5 |
| 52 | 0.76 | 1.3 |
| 56 | 0.69 | 1.44 |
| 61 | 0.71 | 1.41 |
| 67 | 0.71 | 1.4 |
| 6870 | 1.49 | 0.67 |

In order to circumvent the undesired reactions after pegylation, it was decided to block three of the four amine groups of PAMAM Dendrimer (Generation=0) to remove all the hydrogen attached to three primary residual nitrogen atoms. The remaining primary residual nitrogen atom can then be pegylated without any unwanted product. Benzaldehyde and acetophenone were used for above purpose (and almost any aldehyde or ketone can be used for this purpose and an aldehyde substituted cyclodextrin is believed to be especially useful in this respect). As carbonyl group of benzaldehyde and acetophenone reacts with primary residual amine groups of dendrimer (Generation=0) to form an imine. Reactions were carried out using little excess of such reagents. Analysis of the product by NMR indicated that the expected product 5 was formed along with the other side products. Blocking only three residual amine groups out of four was not achieved successfully and was complicated due to distribution of benzaldehyde and acetophenone molecules as well, since side products 9, 10 and others formed along with the expected product 5.

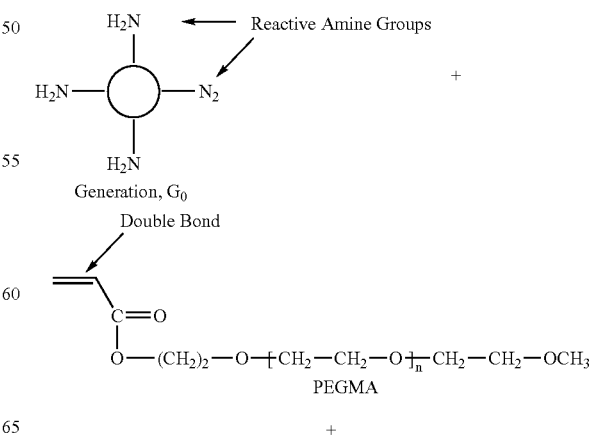

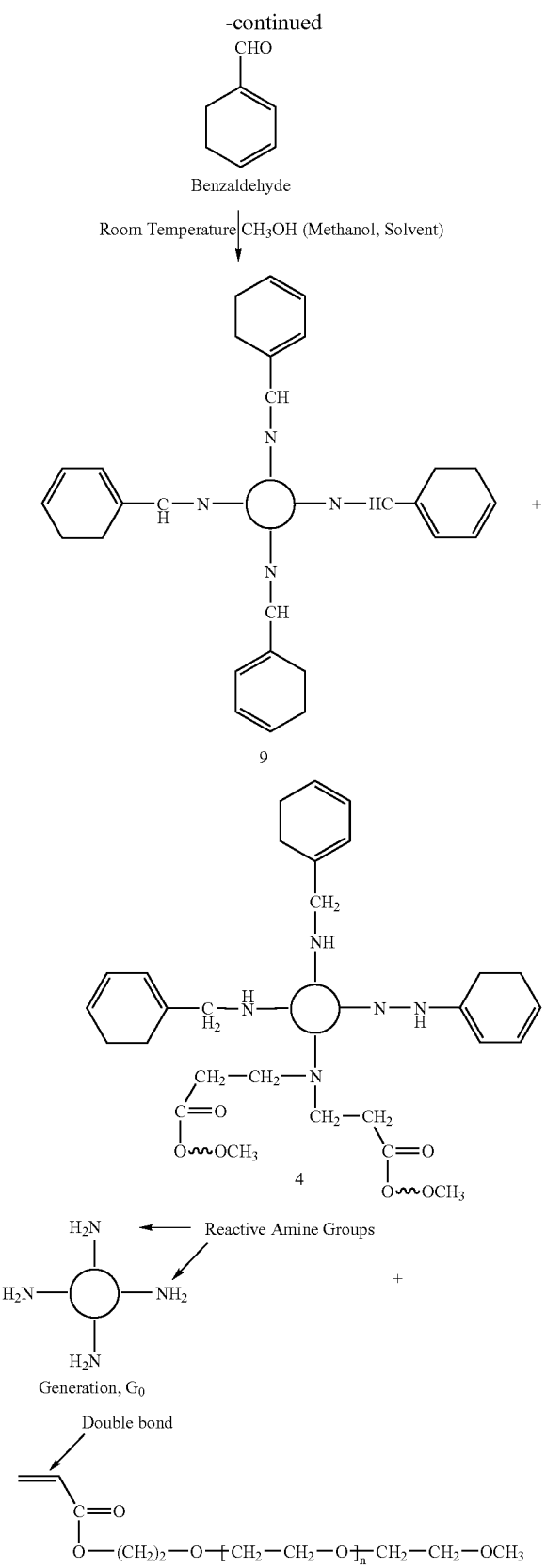

Model reactions 6.a and 6.b show that formation of Schiff base followed by reduction of imine functional group can be achieved. The presence of absorbance at 1642 cm$^{-1}$ confirm the formation of imine. On the other hand the absence of that absorbance in IR spectrum after reduction proved that imine functional group can be reduced. Furthermore, the secondary amine can be pegylated and form the desired product. All the four primary amine groups of dendrimer molecules (Generation=0) can be converted to imine groups by reacting with carbonyl groups of, for example, benzaldehyde as well as acetophenone.

The synthesis routes are shown in scheme 7 and 8 to remove the hydrogen atoms attached to residual primary amine groups. An examination of the spectra reveals the presence of absorbance corresponding to imine functional groups. Analysis of the products by IR and NMR indicates that all amine groups were converted to imines. The imine groups of products 9 and 12 can be reduced by selective reducing agent as dendrimer molecule contains acid amide groups which are very sensitive to reducing agents. Sodium cyanohydridoborate hydride is used for this specific purpose.

An examination of $^1$H and $^{13}$C NMR spectra as well as IR spectra showed that the absence of the absorbance due to imine group. The absorbance of the reduced products 10 and 13 are identified. The hydrogen atoms of compounds 10 and 13 associated with four nitrogen atoms are pegylated in the following step. NMR analysis of the products indicates that compounds 10 as well as 13 were pegylated. The examination of spectral data showed the formation of alcohol of the corresponding aldehyde as side product as excess aldehyde was used for those reactions. In addition, Boron complex compound was formed during the reduction step. Most of the absorbance of the final product in $^1$H and $^{13}$C NMR spectra is identified with the help of $^1$H-$^1$H and $^1$H-$^{13}$C correlation spectra.

It is noticed that reaction schemes 7 as well as 8 can not apparently be accomplished step by step. It is thought necessary that reduced compounds 10 and 13 to be worked up in order to remove unwanted Boron complex compounds after reduction of the imine.

It is observed that reduced product can not be dissolved further in low boiling point solvent such as methanol once solvent was removed after working up. This is apparently because of the formation of intra-molecular H-bonding after the solvent is removed at room temperature under vacuum. This kind of intra-molecular H-bond makes reduced compounds 10 and 13 reluctant to form further inter-molecular H-bonding with solvent. For the sake of simplicity in isolating the product, a low boiling solvent is probably the best choice for this reaction.

Therefore, a modified procedure is developed in order to avoid such solubility problem. The problem associated with solubility is avoided by pegylating compounds 10 and 13 before work up. The analysis of $^1$H NMR indicated that double bonds of PEGMEA are reacted with secondary amine groups of compounds 10 and 13.

The reactions are carried and dendrimers are pegylated first without working it up. Spectral data showed that dendrimer is successfully pegylated. It can be problematic to work up the pegylated products 11 and 14 as cleavage or hydrolysis could have been possible during work up. However, examination of the $^1$H, $^{13}$C NMR spectra showed that the PEG molecules remain unchanged after treatment with strong acid and base. It is observed that delicate ether and carbonyl moieties of pegylated products 11 and 14 are neither cleaved nor hydrolyzed.

Gel electrophoresis of compound 11 and 14 along with different generation of dendrimer (ladder) are carried out to confirm the formation of compounds 11 and 14. The migration of 10 and 11 is slower than that of 13 and 14 and is explained on the basis of steric effects.

Aldehyde substituted beta cyclodextrins are especially useful in the instant invention to block primary amines. For example, an amine terminated polyethylene glycol can be reacted with an aldehyde substituted beta cyclodextrin at room temperature in aqueous sodium cyanohydridoborate to couple the cyclodextrine to the polyethylene glycol via a nitrogen atom to form a pegylated cyclodextrine adduct. Then, the pegylated cyclodextrine adduct can be reacted with the polyoxyalkylene acrylate to form a cyclodextrin adduct that is further pegylated.

Chitosan can be reacted with an aldehyde substituted beta cyclodextrin at room temperature in aqueous sodium cyanohydridoborate to block the primary amines of the chitosan followed by reaction with the polyoxyalkylene acrylate to form a pegylated and beta cyclodextrin substituted chitosan. Peptides, polypeptides and proteins containing primary amines can be reacted with an aldehyde substituted beta cyclodextrin at room temperature in aqueous sodium cyanohydridoborate to block the primary amines of the peptide, polypeptide or protein followed by reaction with the polyoxyalkylene acrylate to form a pegylated and beta cyclodextrin substituted peptide, polypeptide or protein.

As a specific example, the following scheme can be used in the instant invention to first convert the primary amines of poly-L-arginine to secondary amines by the addition of a cyclodextrin to the amine group and then pegylation with a polyethylene glycol acrylate. A 3 necked, 25-mL, round-bottomed, flask is fitted with nitrogen inlet, a condenser with drying tube, a rubber septum, and a magnetic stir bar. The following ingredients are added to the flask: poly-L-arginine hydrochloride (5 mg, 0.663 μmol), beta cyclodextrin monoaldehyde (58.0 mg, 51.2 μmol), 2-mL of deionized water and 1-mL sodium hydroxide solution (0.2586M). Immediately after addition of the base, sodium cyanoborohydride (8.6 mg, 0.137 mmol) is added. The reaction mixture is stirred for 72 hours at room temperature. Half the reaction mixture (1.5-mL) is then removed and precipitated in 5-mL acetone for analysis to confirm the desired reaction. The remainder of the reaction mixture is mixed with 1-mL of poly(ethylene glycol) methyl ether acrylate aqueous solution (0.0286M). The reaction mixture is then stirred for an additional 72 hours at room temperature and then precipitated in 10-mL of acetone and centrifuged to yield a white solid that is dried under vacuum overnight. Analysis of the white solid confirms the desired formation of a pegylated beta cyclodextrin-poly-L-arginine conjugate.

As a specific further example, the following scheme can be used in the instant invention to first convert the primary amines of poly-L-lysine to secondary amines by the addition of a cyclodextrin to the amine group and then pegylation with a polyethylene glycol acrylate. A 3 necked, 25-mL, round-bottomed, flask is fitted with a nitrogen inlet, a condenser with drying tube, a rubber septum and a magnetic stir bar. The following ingredients are added to the flask: poly-$_L$-lysine hydrochloride (8 mg, 0.5 μmol), beta cyclodextrin monoaldehyde (55.0 mg, 48.5 μmol), 2-mL of deionized water and 1-mL sodium hydroxide solution (0.0485M). Immediately after addition of the base, sodium cyanoborohydride (8.1 mg, 0.129 mmol) is added. The reaction mixture is then stirred for 72 hours at room temperature. Half the reaction mixture (1.5-mL) is then removed and precipitated in 5-mL acetone for analysis to confirm the production of the desired product. To the remainder of the reaction mixture, 0.5-mL poly(ethylene glycol)methyl ether acrylate aqueous solution (0.0502M) is added. The reaction mixture is then stirred for an additional 72 hours at room temperature and then precipitated in 10-mL of acetone and centrifuged to yield a white sold that was dried under vacuum overnight. Analysis of the white solid confirms the desired formation of a pegylated beta cyclodextrin-poly-L-lysine conjugate.

As a specific additional example, the following scheme can be used in the instant invention to first convert the primary amines of Chitosan to secondary amines by the addition of a cyclodextrin to the amine group and then pegylation with a polyethylene glycol acrylate. A 3 necked, 25-mL, round-bottomed, flask is fitted with a nitrogen inlet, a condenser with drying tube, a rubber septum and a magnetic stir bar. The following ingredients are added to the flask: low molecular weight chitosan (50 mg, 0.185 mmol) dissolved in 15-mL of 0.1M hydrochloric acid, 2.00 g of beta-glucero-phosphate dissolved in 4-mL of deionized water, beta cyclodextrin monoaldehyde (421 mg, 0.370 mmol) and sodium cyanoborohydride (33 mg, 0.525 mmol). The reaction mixture is then stirred for 72 hours at room temperature. 14-mL of the reaction mixture is removed for analysis to confirm the production of the desired product. To the remainder of the reaction mixture, 4.50-mL poly(ethylene glycol)methyl ether acrylate aqueous solution (0.0220M) is added. The reaction mixture is then stirred for and additional 72 hours at room temperature. The resulting solution is then lyophilized to yield a white fibrous solid. The solid is then washed with acetone using a Soxhlet and dried under vacuum overnight. Analysis of the solid confirms the formation of the desired pegylated beta cyclodextrin-chitosan conjugate.

As a yet further specific additional example, the following scheme can be used in the instant invention to pegylate glutathione. Glutathione (0.153 g, 0.0005 mole), poly (ethylene glycol)methyl ether acrylate (0.225 g, 0.0005 mole) are dissolved in 4 mL of a buffer solution (pH=5.8) in a screw cap vial. The clear aqueous solution is allowed to mix on a table-top shaker for 3 h at room temperature. The entire reaction mixture is lypholized to produce the desired pegylated glutathione.

The following scheme can be used in the instant invention for the pegylation of proteins: (a) the protein is dissolved or dispersed in 0.1M bicarbonate buffer, pH 9.1 (the concentration of proteins as a rule can be measured from their extinction coefficients at 280 nm); (b) mPEG acrylate solutions are prepared at various concentrations in 0.1M bicarbonate buffer, pH 9.1; (c) a known volume of the protein solution is mixed with the mPEG solution in various vials to yield various amino/mPEG ratios; (d) samples are incubated under defined temperatures and times with appropriate control tubes; and (e) after reaction, the reaction mixture is subjected to native gel electrophoresis in 10% polyacrylamide gels (protein staining, as a rule, is performed with Coomassie Blue).

As a final additional specific example, the following scheme can be used in the instant invention to first convert the primary amines of a PAMAM dendrimer to secondary amines by the addition of a cyclodextrin to the amine group and then pegylation with a polyethylene glycol acrylate. A 3 necked, 25-mL, round-bottomed, flask is fitted with a nitrogen inlet, a condenser with drying tube, a rubber septum and a magnetic stir bar. The following ingredients are added to the flask: PAMAM generation 0 dendrimer (160 mg, 0.310 mmol) dissolved in 1-mL deionized water, beta cyclodextrin monoaldehyde (1.5010 g, 1.32 mmol) dissolved in 15-mL of deionized water and sodium cyanoborohydride (229.6 mg, 3.65 mmol). The reaction mixture is then stirred for 72 hours at room temperature. 6-mL of the reaction mixture is then removed and precipitated in methanol to confirm the production of the desired product. To the remainder of the reaction mixture, 9-mL poly(ethylene glycol) methyl ether acrylate aqueous solution (0.0880M) are added. The reaction mixture is then stirred for an additional 72 hours at room temperature and then precipitated in 10-mL of acetone and centrifuged to yield a white sold that was dried under vacuum overnight. Analysis confirms the desired production of pegylated beta cyclodextrin PAMAM dendrimer conjugate.

Thus, it should be appreciated that in the instant invention any compound containing an amine group can be reacted with the polyoxyalkylene acrylate to form a conjugate comprising a polyoxyalkylene sub-structure. Furthermore, when the amine group is a primary amine, then it may be necessary (such as in the case of a PAMAM dendrimer) as a preliminary step to "block" the primary amine(s), as discussed above in detail, by reaction of such primary amine(s) with an aldehyde or ketone followed by conversion of the resulting imine to a secondary amine. Many drug compounds contain amine group(s) and it should be understood that the instant invention is an excellent means of converting such drugs to a polyoxyalkylene conjugate of the drug.

The term "polyoxyalkylene" is defined in the above referenced U.S. Pat. No. 6,280,745, herein fully incorporated by reference, and includes polyethylene glycol, polypropylene glycol, as well as block and random polyethylene glycol/polypropylene glycol co-polymers. Although acrylate terminated polyethylene glycols are commercially available, acrylate terminated polyethylene glycol can be prepared, for example, by reacting a monomethoxy polyethylene glycol with acryloyl chloride or, for example, with methacroloyl chloride.

The molecular weight of the polyoxyalkylene sub-structure of the instant invention can be tailored so that the conjugate has desired properties such as solubility characteristics that are more compatible with the biologic system. In many cases, the preferred molecular weight of the polyoxyalkylene sub-structure of the instant invention will be in the range of from about 500 to about 5000 grams per mole.

In addition to reactions with amines, the acrylate terminated polyoxyalkylene of the instant invention also can be reacted with a terminal sulfur (sulfide) group(s) of a biologically active compound to produce novel compounds. For example an aqueous buffered (pH=5.8) solution of glutathione can be pegylated at room temperature by a two hour reaction with the acrylate terminated polyethylene glycol of the instant invention. Polycysteine can be similarly pegylated.

The process of the instant invention produces novel compounds that, as expected, maintain their biological activity. For example, bovine erythrocyte carbonic anhydrase (CAB) pegylated with mPEG acrylate at room temperature in a pH 9.1 aqueous buffer (mole ratio of CAB to mPEG acrylate of 1:8; 1:2 and 8:1) maintains its biological activity. As a further example, hen egg white lysozyme (HEWL) pegylated with mPEG acrylate at room temperature in a pH 9.1 aqueous buffer (mole ratio of HEWL to mPEG acrylate of 1:2 and 8:1) also maintains its biological activity.

What is claimed is:

1. A compound having the formula:

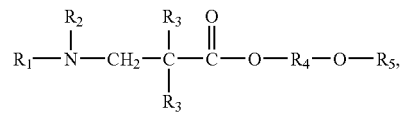

wherein:
R$_1$-N is a dendrimer or a protein having a terminal or pendant amine,
R$_2$ is an organic radical derived from benzyaldehyde,
each R$_3$ is H,
R$_4$ is a polyoxyalkylene radical derived from polyethylene gycol, and R$_5$ is CH$_3$.

2. The compound of claim 1, wherein R$_1$ is a protein.

3. The compound of claim 1, wherein R$_1$ is a dendrimer.

4. A method of making the compound of claim 1 comprising the step of reacting a compound:
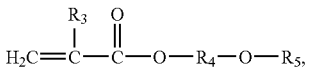
with a compound:
H₂C=C(R₃)−C(=O)−O−R₄−O−R₅,
thereby forming the compound
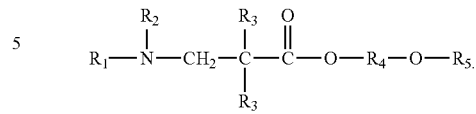
5. The compound of claim 4, wherein $R_1$ is a protein.
6. The compound of claim 4, wherein $R_1$ is a dendrimer.
* * * * *